United States Patent [19]

Kondo et al.

[11] Patent Number: 5,633,303
[45] Date of Patent: May 27, 1997

[54] ORGANOPOLYSILOXANE GUM EMULSION

[75] Inventors: Hidetoshi Kondo; Tadashi Hamachi; Hidehiko Hosokawa; Fumitaka Suto; Junichi Maeshima, all of Chiba Prefecture, Japan

[73] Assignee: Dow Corning Toray Silicone Co., Ltd., Tokyo, Japan

[21] Appl. No.: 586,507

[22] Filed: Jan. 11, 1996

[30] Foreign Application Priority Data

Jan. 12, 1995 [JP] Japan ................... 7-019798
Jul. 28, 1995 [JP] Japan ................... 7-212669

[51] Int. Cl.$^6$ .................................. C08K 3/20
[52] U.S. Cl. ................. 524/268; 524/457; 524/588
[58] Field of Search .......................... 524/588, 457, 524/268; 424/401

[56] References Cited

U.S. PATENT DOCUMENTS

| | | | |
|---|---|---|---|
| 4,431,452 | 2/1984 | Comper et al. | 106/38.22 |
| 4,788,001 | 11/1988 | Narula | 252/312 |
| 5,039,724 | 8/1991 | Demlehner et al. | 524/267 |
| 5,064,916 | 11/1991 | Sasaki et al. | 525/478 |
| 5,145,932 | 9/1992 | Sasaki et al. | 528/15 |
| 5,177,131 | 1/1993 | Takago et al. | 524/100 |
| 5,415,860 | 5/1995 | Beucherie et al. | 424/401 |

FOREIGN PATENT DOCUMENTS

| | | |
|---|---|---|
| 200916 | 11/1986 | European Pat. Off. . |
| 366133 | 5/1990 | European Pat. Off. . |
| 522899 | 1/1993 | European Pat. Off. . |
| 230309 | 8/1992 | Japan . |
| 7069844 | 3/1995 | Japan . |
| 2087913 | 6/1982 | United Kingdom . |
| 2289686 | 11/1995 | United Kingdom . |

OTHER PUBLICATIONS

JIS C 2123–1986, Test Methods for Silicone Rubber Compounds for Electrical Applications.
Derwent AN 95–1444672.

*Primary Examiner*—Melvyn I. Marquis
*Assistant Examiner*—Karen A. Dean
*Attorney, Agent, or Firm*—James L. DeCesare

[57] ABSTRACT

An organopolysiloxane gum emulsion is afforded by the emulsification of an organopolysiloxane gum in water. The organopolysiloxane gum emulsion is useful as a cosmetic base, lustrant, lubricant, antifoam, fiber-treatment agent, and paint additive. The organopolysiloxane gum emulsion includes (A) 100 weight parts organopolysiloxane gum whose plasticity at 25° C. is at least 0.75 mm, (B) 1 to 100 weight parts emulsifying agent, and (C) 3 to 800 weight parts water.

12 Claims, No Drawings

ORGANOPOLYSILOXANE GUM EMULSION

BACKGROUND OF THE INVENTION

This invention relates to organopolysiloxane gum emulsions. More particularly, this invention relates to an organopolysiloxane gum emulsion that can be used as a cosmetic base, lustrant, lubricant, antifoam, fiber-treatment agent, and paint additive.

Emulsions of high-viscosity organopolysiloxanes are used as cosmetic bases, lustrants, antifoams, lubricants, and fiber-treatment agents. These emulsions of high-viscosity organopolysiloxanes have generally been prepared by the strong acid-catalyzed or strong base-catalyzed emulsion polymerization of an organosiloxane oligomer having a low degree of polymerization (DP) i.e. Japanese Patent Publication Numbers Sho 34-2041 [2,041/1959] and Sho 41-13995 [13,995/1966].

However, due to the use of a strong acid or strong base as the polymerization catalyst, the emulsions afforded by these emulsion polymerization methods take the form of very highly ionic anionic or cationic emulsions. One problem with these emulsions is that their stability is strongly impaired when they are employed in combination with counterionic additives. Moreover, these methods provide poor control over the DP of the organopolysiloxane making up the emulsion, and they also suffer from limitations in terms of DP. These problems have resulted in attempts at emulsion preparation by emulsification by mechanical means of organopolysiloxanes already having a high viscosity. Unfortunately, it has generally proven to be quite difficult to prepare stable emulsions by the emulsification in water of high-viscosity organopolysiloxanes. Attempts have been made to first reduce the viscosity by dissolving the high-viscosity organopolysiloxane in a suitable diluting solvent, and then carrying out emulsification using a mechanical agitator such as a colloid mill, or homogenizer. However, the resulting emulsion necessarily contains the diluting solvent, which can impair the properties expected from the high-viscosity organopolysiloxane in the ultimate application. This problem prevents the use of these emulsions in some applications.

Japanese Patent Publication Number Sho 46-10162 [10, 162/1971] teaches the homogenization of a dimethylpolysiloxane oil (viscosity at 25° C.=500,000 centistokes), emulsifying agent, and water by mixing on a three-roll mill followed by dilution of the resulting mixture with water. No mention is made, however, of emulsions of organopolysiloxane gums, whose viscosities at 25° C. exceed 1,000,000 centistokes. Japanese Patent Application Laid Open [Kokai or Unexamined] Number Hei 4-230309 [230,309/1992] in Examples 1–3 discloses examples of emulsion preparation by mixing a dimethylpolysiloxane with a viscosity at 25° C. of 1,000,000 centistokes, emulsifying agent, and water in a homomixer. Also disclosed therein are Examples 4–6 of emulsion preparation by mixing in a homomixer, water, emulsifying agent, a low-viscosity dimethylpolysiloxane oil, and a dimethylpolysiloxane gum with a viscosity at 25° C. of 7,000,000 centistokes or 10,000,000 centistokes.

One drawback to the emulsions of the high-viscosity dimethylpolysiloxane as disclosed in Japanese Patent Application Laid Open [Kokai or Unexamined] Number Hei 4-230309 [230,309/1992] is their low dimethylpolysiloxane content of 0.1 to 10 weight%. In regard to the dimethylpolysiloxane emulsions of Examples 1 to 3, these have a poor stability, with the result that the water and high-viscosity dimethylpolysiloxane separate when these emulsions are allowed to stand for long periods of time. Drawbacks can occur with the dimethylpolysiloxane emulsions of Examples 4 to 6 because they contain dimethylpolysiloxane oil. For example, the use of such emulsions as a cosmetic base results in a poor resistance to washing, and in sensations of refreshment and lightness that are weak, and in particular not longlasting. When used as lustrants, such emulsions give an unsatisfactory luster durability, and when used as water repellents, they give a poorly durable water repellency. These drawbacks place limitations on the use of these emulsions.

We discovered that the use of a mixing device equipped with a special agitation mechanism makes possible the easy preparation of emulsions of very high-DP high-viscosity organopolysiloxanes, i.e., organopolysiloxane gums. This method has been disclosed in our Japanese Patent Application Number Hei 7-9248 [9,248/1995]. The present invention was achieved based on the discovery that the emulsions afforded by this method solve the problems described hereinbefore.

BRIEF SUMMARY OF THE INVENTION

The present invention takes as its object an organopolysiloxane gum emulsion that is afforded by the emulsification of an organopolysiloxane gum in water, and in particular which can be used as a cosmetic base, lustrant, lubricant, antifoam, fiber-treatment agent, of paint additive.

This object is achieved by an organopolysiloxane gum emulsion that characteristically comprises (A) 100 weight parts of an organopotysiloxane gum whose plasticity at 25° C. is at least 0.75 mm wherein said plasticity is measured according to the plasticity measurement method described in Japanese Industrial Standard C 2123, (B) 1 to 100 weight parts of an emulsifying agent, and (C) 3 to 800 weight parts of water. The emulsion is made by the emulsification of component (A) in component (C), by means of component (B), and has a component (A) content of 11 to 95 weight%.

These and other objects of the invention will become apparent from a consideration of the detailed description.

DETAILED DESCRIPTION

The organopolysiloxane gum (A) is the base ingredient of the emulsion. It must have a plasticity at 25° C. of at least 0.75 mm, and plasticities from 1.0 mm to 2.5 mm are preferred. As used herein, plasticity is the value measured at 25° C. according to Japanese Industrial Standard (JIS) C 2123. These organopolysiloxane gums are known as the base polymers for silicone rubbers and are generally regarded as having viscosities at 25° C. in excess of $10^6$ centistokes. Organopolysiloxane gums are exemplified by dimethylpolysiloxane gums, dimethylsiloxane-phenylmethylsiloxane copolymer gums, dimethylsiloxane-diphenylsiloxane copolymer gums, and dimethylsiloxane-vinylmethylsiloxane copolymer gums. The molecular chain terminals of the organopolysiloxane gums are ordinarily endblocked by the trimethylsiloxy group, dimethylhydroxysiloxy group, or dimethylvinylsiloxy group. The organopolysiloxane gums may optionally contain additives such as silica micropowder.

The emulsifying agent component (B) is exemplified by nonionic surfactants, anionic surfactants, and cationic surfactants. Nonionic surfactants are exemplified by polyoxyalkylene alkyl ethers, polyoxyalkylene alkylphenol ethers, polyoxyalkylene alkyl esters, polyoxyalkylene sorbitan alkyl esters, polypropylene glycols, and diethylene glycol. Anionic surfactants are exemplified by the salts of higher fatty acids such as sodium laurate, sodium stearate, sodium oleate, and sodium linolenate; alkylbenzenesulfonic acids such as hexylbenzenesulfonic acid, octylbenzenesulfonic acid, decylbenzenesulfonic acid, dodecylbenzenesulfonic acid, cetylbenzenesulfonic acid, myristylbenzenesulfonic acid, and the salts thereof; sulfate esters of polyoxyethylene monoalkyl ethers such as $CH_3(CH_2)_6CH_2O(C_2H_4O)_2SO_3H$, $CH_3(CH_2)_8CH_2O(C_2H_4O)_8SO_3H$, $CH_3(CH_2)_{19}CH_2O(C_2H_4O)_4SO_3H$, $CH_3(CH_2)_8CH_2C_6H_4O(C_2H_4)_2SO_3H$; and alkylnaphthylsulfonic acids and their salts. Cationic surfactants are exemplified by quaternary ammonium hydroxides such as octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, didodecyldimethylammonium hydroxide, dioctadecyldimethylammonium hydroxide, beef tallow trimethylammonium hydroxide, cocotrimethylammonium hydroxide, and their salts. The nonionic surfactants are preferred for use in the present invention.

Component (B) is used at 1 to 100 weight parts, preferably at 1 to 30 weight parts, and more preferably at 3 to 20 weight parts, in each case per 100 weight parts component (A).

The water component (C) is the dispersing medium in which component (A) is emulsified and dispersed in the presence of component (B). Component (C) is used at 3 to 800 weight parts and preferably 3 to 570 weight parts, in each case per 100 weight parts component (A).

The organopolysiloxane gum emulsion according to the present invention is an organopolysiloxane gum emulsion comprising the above-described components (A), (B), and (C). It is made by emulsification of the organopolysiloxane gum (A) in the water (C) under the influence of the emulsifying agent (B). Its average particle diameter will generally be from 0.1 to 50 micrometers.

Other ingredients may be mixed into the organopolysiloxane gum emulsions in addition to the components (A), (B), and (C). Some examples are the salts of carboxylic acids with metals such as iron, cerium, titanium, calcium, and zirconium; organoamine compounds such as triethanolamine, triethylenediamine, and dimethylphenylamine; preservatives; colorants; resin processing agents such as glyoxal resins, melamine resins, urea resins, polyester resins, and acrylic resins; rubber latexes such as styrene-butadiene latexes and natural rubber latexes; organohydrogenpolysiloxane emulsions; and organoalkoxysilane emulsions.

The organopolysiloxane gum emulsions according to the present invention must contain 11 to 95 weight% component (A) and preferably contain from 15 to 95 weight% component (A) and more preferably contain from 20 to 95 weight% component (A).

Emulsions according to the present invention can be prepared, for example, by first homogeneously mixing the prescribed quantity of emulsifying agent (B) and a portion of the water (C) into the prescribed quantity of organopolysiloxane gum (A), using a mixer equipped with a high-shear mechanism, and thereafter homogeneously blending the remaining water into the resulting mixture to make an emulsion with a concentration appropriate to its specific application.

Organopolysiloxane gum emulsions according to the present invention are useful as cosmetic bases, lustrants, antifoams, fiber-treatment agents, lubricants, release agents, and paint additives.

The present invention will be explained in greater detail below through working examples, in which "parts" denotes "weight parts" and "%" denotes "weight%". The plasticity was measured in accordance with the method described in JIS C 2123, whose details are given below.

Method for measuring the plasticity (1) An organopolysiloxane gum test specimen was prepared and placed between 2 sheets of cellophane. Each test specimen was a sphere weighing 4.2±0.05 g with a diameter of 2 cm, and three test specimens were prepared. Each test specimen was held for 15 minutes at 25° C.

(2) The test specimen was placed between parallel plates thermostatted to 25° C. and a load of 1 kg was applied from the top. After 3 minutes the scale on the dial gage was read to hundredths of millimeters and the height of the test specimen was recorded. This value was taken as the plasticity of the test specimen.

(3) The average of the values measured on the three test specimens is used below as the plasticity.

EXAMPLE 1

The following were mixed in a high-shear mixer to yield a transparent paste: 60.0 parts trimethylsiloxy-endblocked dimethylpolysiloxane gum as component (A) (plasticity at 25° C.=1.24 mm, viscosity at 25° C.=10,940,000 centistokes), 2.5 parts polyoxyethylene (4) lauryl ether, 3.5 parts polyoxyethylene (25) lauryl ether, 0.2 part sodium polyoxyethylene (4) lauryl ether sulfate, and 3 parts pure water (ion-exchanged). The high-shear mixer contained 2 shearing-stirring mechanisms installed serially within a cylindrical casing between the inlet and outlet of the casing, wherein each shearing-stirring mechanism consisted of a turbine-type rotor having a plural number of spiral blades paired with a stator installed around the circumference of the turbine-type rotor. This mixing was followed by the addition of 30.8 parts pure water to the paste with mixing to homogeneity to give an emulsion that contained 60 weight% dimethylpolysiloxane gum. The dimethylpolysiloxane gum was emulsified in the water, and its average particle diameter was 0.5 micrometer. No separation of the dimethylpolysiloxane gum from the water was observed even after this emulsion had been allowed to stand for 1 month.

EXAMPLE 2

The following were mixed in a high-shear mixer to yield a transparent paste: 60.0 parts trimethylsiloxy-endblocked dimethylpolysiloxane gum as component (A) (plasticity at 25° C.=2.01 mm, viscosity at 25° C. at least 15,000 centistokes), 2.5 parts polyoxyethylene (4) lauryl ether, 3.5parts polyoxyethylene (25) lauryl ether, 0.2 part cetyltrimethylammonium chloride, and 3 parts pure water (ion-exchanged). The high-shear mixer was a mixer that contained 2 shearing-stirring mechanisms installed serially within a cylindrical casing between the inlet and outlet of the casing, wherein each shearing-stirring mechanism consisted of a turbine-type rotor having a plural number of spiral blades paired with a stator installed around the circumference of the turbine-type rotor. This mixing was followed by the addition of 30.8 parts pure water to the paste with mixing to homogeneity to give an emulsion that contained 60 weight% dimethylpolysiloxane gum. The dimethylpolysiloxane gum was emulsified in the water, and its average particle diameter was 1 micrometer. No separation of the dimethylpolysiloxane gum from the water was observed even after this emulsion had been allowed to stand for 1 month.

Comparative Example 1

The following were mixed in a homomixer to yield an emulsion that contained 60 weight% dimethylpolysiloxane oil: 60.0 parts trimethylsiloxy-endblocked dimethylpolysiloxane oil as component (A) (plasticity at 25° C=0.73 mm, viscosity at 25° C.=1,000,000 centistokes), 2.5 parts polyoxyethylene (4) lauryl ether, 3.5 parts polyoxyethylene (25) lauryl ether, 0.2 part sodium polyoxyethylene (4) lauryl ether sulfate, and 33.8 parts pure water (ion-exchanged). The dimethylpolysiloxane oil was emulsified in the water, and its average particle diameter was 1 micrometer. Separation of the organopolysiloxane oil from the water was observed after this emulsion had been allowed to stand for 1 day.

Application Example 1

Application in a skin lotion

A skin lotion was prepared by blending 2 weight% (as dimethylpolysiloxane component) of the organopolysiloxane gum emulsion prepared in Example 1 into a skin lotion (moisturizing cream) whose main ingredients were microcrystalline wax, vaseline, lipophilic glycerol monooleate, and water. This skin lotion was applied to the arm of a panelist, and the arm was then washed with soapy water. Washing was followed by measurement of the amount of residual organopolysiloxane component on the arm. This washing with soapy water was carried out by gently rubbing with the hand 30 times. The amount of organopolysiloxane component remaining on the skin was measured as the percentage remaining, using the change in the ratio between the absorbance at 1260 cm$^{-1}$ indicative of SiMe and the absorbance at 1540 cm$^{-1}$ indicative of the amide II band of protein in infrared absorption spectral analysis. The results are reported in Table 1. A comparative skin lotion was similarly prepared, but in this case, replacing the trimethylsiloxy-endblocked dimethylpolysiloxane gum emulsion with 2 weight% (as dimethylpolysiloxane component) of an emulsion of a trimethylsiloxy-endblocked dimethylpolysiloxane with a viscosity at 25° C. of 30,000 centistokes. This emulsion used in the comparative skin lotion was prepared as in Example 1, but using a trimethylsiloxy-endblocked dimethylpolysiloxane oil with a viscosity at 25° C. of 30,000 centistokes in place of the trimethylsiloxy-endblocked dimethylpolysiloxane gum that was used in Example 1. The performance of this comparative skin lotion was measured as above, and these measurement results are also reported in Table 1 as Comparative Example 1.

TABLE 1

|  | 0 (initial) | after first wash | after second wash |
| --- | --- | --- | --- |
| Application Example 1 | 100% | 70% | 50% |
| Comparative Example 1 | 100% | 30% | 25% |

Application Example 2

Application in a car body wax

A car body wax was prepared by blending 2 weight% (as dimethylpolysiloxane component) of the dimethylpolysiloxane gum emulsion prepared in Example 1 into an emulsion-type semi-mixed wax whose main components were mineral spirit, polyethylene wax, dimethylpolysiloxane oil with a viscosity at 25° C. of 500 centistokes, oleic acid, morpholine, and water. This wax was applied to a car body, which was then left undisturbed outdoors for one month. The water repellency and soiling of the treated surface were then evaluated, and these results are reported in Table 2. A comparative car body wax was similarly prepared, but in this case replacing the trimethylsiloxy-endblocked dimethylpolysiloxane gum emulsion with 2 weight% (as dimethylpolysiloxane component) of an emulsion of a trimethylsiloxy-endblocked dimethylpolysiloxane with a viscosity at 25° C. of 30,000 centistokes. This emulsion used in the comparative car body wax was prepared as in Example 1, but using a trimethylsiloxy-endblocked dimethylpolysiloxane oil with a viscosity at 25° C. of 30,000 centistokes in place of the trimethylsiloxy-endblocked dimethylpolysiloxane gum that was used in Example 1. The performance of this comparative car body wax was measured as above, and these measurement results are also reported in Table 2 as Comparative Example 2.

TABLE 2

|  | water repellency immediately after application | after exposure outdoors for 1 month | |
| --- | --- | --- | --- |
|  |  | water repellancy | soiling |
| Application Example 2 | good | good | good |
| Comparative Example 2 | good | poor | poor |

Application Example 3

Application to a conditioning shampoo

A conditioning shampoo was prepared by blending 2 weight% (as dimethylpolysiloxane component) of the dimethylpolysiloxane gum emulsion prepared in Example 2 into a shampoo whose main components were an alkyl sulfate, a cationic cellulose derivative, and water. Hair was washed with this shampoo, dried, and then subjected to sensory evaluation. These results are reported in Table 3. A comparative conditioning shampoo was similarly prepared, but in this case replacing the trimethylsiloxy-endblocked dimethylpolysiloxane gum emulsion with 2 weight% (as dimethylpolysiloxane component) of an emulsion of a trimethylsiloxy-endblocked dimethylpolysiloxane with a viscosity at 25° C. of 100,000 centistokes. This emulsion used in the comparative conditioning shampoo was prepared as in Example 2, but using a trimethylsiloxy-endblocked dimethylpolysiloxane oil with a viscosity at 25° C. of 100,000 centistokes in place of the trimethylsiloxy-endblocked dimethylpolysiloxane gum that was used in Example 2. The performance of this comparative conditioning shampoo was measured as above, and these measurement results are also reported in Table 3 as Comparative Example 3.

TABLE 3

| | feel of hair after washing and drying |
|---|---|
| Application Example 3 | the hair is light and not sticky and is soft to riffling with the fingers |
| Comparative Example 3 | the hair has a slightly sticky feel and is stiff to riffling with the fingers |

The organopolysiloxane gum emulsion according to the present invention is a very storage-stable emulsion. In particular, because the base ingredient of this emulsion is an organopolysiloxane gum (A), it has characteristics not found in prior emulsions of high-viscosity organopolysiloxane oils. For example, when our emulsion is used as a cosmetic base, it yields a cosmetic that provides the refreshing sensation unique to organopolysiloxane gums and does so with an excellent persistence. When used as a lustrant, lubricant, release agent, or antifoam with various substrates, the emulsion is characterized by the ability to give a highly persistent or robust lubrication, release performance, and antifoam performance.

Other variations may be made in the compounds, compositions, and methods described without departing from the essential features of the invention. The forms of invention are exemplary and not limitations on its scope as defined in the claims.

We claim:

1. An emulsion comprising (A) 100 parts by weight of an organopolysiloxane gum with a plasticity value at 25° C. of at least 0.75 mm, the value being determined according to Japanese Industrial Standard JIS C 2123-1986; (B) 1–100 parts by weight of an emulsifying agent per 100 parts by weight of the gum; and (C) 3–800 parts by weight of water per 100 parts by weight of the gum; the emulsion being made by emulsifying the gum in water with the emulsifying agent, with the proviso that at least 11 percent of the gum is present in the emulsion.

2. An emulsion according to claim 1 in which the gum has a viscosity of at least ten million Centistokes.

3. An emulsion according to claim 1 in which the gum has a viscosity of at least fifteen million Centistokes.

4. A skin lotion, car body wax, or conditioning shampoo, containing the emulsion defined according to claim 1.

5. An emulsion comprising (A) 100 parts by weight of an organopolysiloxane gum with a plasticity value at 25° C. of 1–2.5 mm, the value being determined according to Japanese Industrial Standard JIS C 2123-1986(B) 1–100 parts by weight of an emulsifying agent per 100 parts by weight of the gum; and (C) 3–800 parts by weight of water per 100 parts by weight of the gum; the emulsion being made by emulsifying the gum in water with the emulsifying agent, with the proviso that at least 15 percent of the gum is present in the emulsion.

6. An emulsion according to claim 5 in which the gum has a viscosity of at least ten million Centistokes.

7. An emulsion according to claim 5 in which the gum has a viscosity of at least fifteen million Centistokes.

8. A skin lotion, car body wax, or conditioning shampoo, containing the emulsion defined according to claim 5.

9. An emulsion comprising (A) 100 parts by weight of an organopolysiloxane gum with a plasticity value at 25° C. of 1–2.5 mm, the value being determined according to Japanese Industrial Standard JIS C 2123-1986; (B) 1–100 parts by weight of an emulsifying agent per 100 parts by weight of the gum; and (C) 3–800 parts by weight of water per 100 parts by weight of the gum; the emulsion being made by emulsifying the gum in water with the emulsifying agent, with the proviso that at least 15 percent of the gum is present in the emulsion.

10. An emulsion according to claim 9 in which the gum has a viscosity of at least ten million Centistokes.

11. An emulsion according to claim 9 in which the gum has a viscosity of at least fifteen million Centistokes.

12. A skin lotion, car body wax, or conditioning shampoo, containing the emulsion defined according to claim 9.

* * * * *